US010515722B2

(12) United States Patent
Vahlberg

(10) Patent No.: US 10,515,722 B2
(45) Date of Patent: Dec. 24, 2019

(54) MEDICAL EQUIPMENT WITH DIVERSION MECHANISM

(71) Applicant: Omnicell, Inc., Mountain View, CA (US)

(72) Inventor: John Vahlberg, Mountain View, CA (US)

(73) Assignee: Omnicell, Inc., Mountain View, CA (US)

( * ) Notice: Subject to any disclaimer, the term of this patent is extended or adjusted under 35 U.S.C. 154(b) by 373 days.

(21) Appl. No.: 14/883,938

(22) Filed: Oct. 15, 2015

(65) Prior Publication Data

US 2017/0109480 A1  Apr. 20, 2017

(51) Int. Cl.
*G16H 40/20* (2018.01)
*A61J 7/00* (2006.01)
(Continued)

(52) U.S. Cl.
CPC ............ *G16H 40/20* (2018.01); *A61J 7/0084* (2013.01); *G06F 16/24578* (2019.01); *G06F 19/3462* (2013.01); *G07F 11/002* (2013.01)

(58) Field of Classification Search
CPC ...... G06Q 50/22; G06Q 50/24; G06F 19/322; G06F 19/3462; G16H 40/20; G16H 40/40; G16H 20/13
See application file for complete search history.

(56) References Cited

U.S. PATENT DOCUMENTS 5,190,185 A   3/1993  Blechl
5,377,864 A   1/1995  Blechl et al.
(Continued)

FOREIGN PATENT DOCUMENTS

WO   2014/085235 A1   6/2014
WO   2014/127234 A1   8/2014

OTHER PUBLICATIONS

Epstein, Richard H., David M. Gratch, and Zvi Grunwald. "Development of a scheduled drug diversion surveillance system based on an analysis of atypical drug transactions." Anesthesia & Analgesia 105.4 (2007): 1053-1060. (Year: 2007).*

(Continued)

*Primary Examiner* — Jonathan Durant
(74) *Attorney, Agent, or Firm* — Kilpatrick Townsend & Stockton LLP

(57) ABSTRACT

A method for identifying medical diverters includes identifying users having similar job functions. Use data indicative of user access to a medication dispensing system is retrieved and is analyzed to identify periods of use of the system for users. Boundaries of work shifts are determined and users are organized into work shifts based on periods of use. A comparison period is determined. Diversion data indicative of behavior associated with diversion for each user is identified. A diversion score indicative of a likelihood that a user is diverting medication is generated by averaging the data by shifts worked for each user and statistically comparing the averaged data. Diversion scores are combined for a medication type to generate a group score. A consistency factor is determined and an overall score is generated. A determination whether any overall scores exceed an overall threshold is made. Users whose score exceeds the threshold are flagged.

19 Claims, 9 Drawing Sheets

(51) Int. Cl.
*G06F 19/00* (2018.01)
*G06F 16/2457* (2019.01)
*G07F 11/00* (2006.01)

(56) References Cited

U.S. PATENT DOCUMENTS

| | | |
|---|---|---|
| 5,745,366 A | 4/1998 | Higham et al. |
| 5,805,455 A | 9/1998 | Lipps |
| 5,805,456 A | 9/1998 | Higham et al. |
| 5,905,653 A | 5/1999 | Higham et al. |
| 5,927,540 A | 7/1999 | Godlewski |
| 6,011,999 A | 1/2000 | Holmes |
| 6,039,467 A | 3/2000 | Holmes |
| 6,151,536 A | 11/2000 | Arnold et al. |
| 6,170,929 B1 | 6/2001 | Wilson et al. |
| 6,272,394 B1 | 8/2001 | Lipps |
| 6,385,505 B1 | 5/2002 | Lipps |
| 6,609,047 B1 | 8/2003 | Lipps |
| 6,640,159 B2 | 10/2003 | Holmes et al. |
| 6,760,643 B2 | 7/2004 | Lipps |
| 6,776,304 B2 | 8/2004 | Liff et al. |
| 6,975,922 B2 | 12/2005 | Duncan et al. |
| 7,218,231 B2 | 5/2007 | Higham |
| 7,249,688 B2 | 7/2007 | Hunter et al. |
| 7,348,884 B2 | 3/2008 | Higham |
| 7,554,449 B2 | 6/2009 | Higham |
| 7,571,024 B2 | 8/2009 | Duncan et al. |
| 7,588,167 B2 | 9/2009 | Hunter et al. |
| 7,675,421 B2 | 3/2010 | Higham |
| 7,734,369 B2 | 6/2010 | Godlewski et al. |
| 7,835,819 B2 | 11/2010 | Duncan et al. |
| 7,979,310 B2 | 7/2011 | Pujar et al. |
| 8,073,563 B2 | 12/2011 | Vahlberg et al. |
| 8,126,590 B2 | 2/2012 | Vahlberg et al. |
| 8,131,397 B2 | 3/2012 | Vahlberg et al. |
| 8,140,186 B2 | 3/2012 | Vahlberg et al. |
| 8,155,786 B2 | 4/2012 | Vahlberg et al. |
| 8,239,062 B2 | 8/2012 | Vahlberg et al. |
| 8,280,550 B2 | 10/2012 | Levy et al. |
| 8,378,620 B2 | 2/2013 | Reckelhoff |
| 8,416,080 B2 | 4/2013 | Higham |
| 8,484,049 B2 | 7/2013 | Mullenger et al. |
| 8,773,270 B2 | 7/2014 | Paydar et al. |
| 8,812,153 B2 | 8/2014 | Reckelhoff |
| 9,042,607 B2 | 5/2015 | Chai et al. |
| 9,158,892 B2 | 10/2015 | Levy et al. |
| 2003/0171998 A1 | 9/2003 | Pujar et al. |
| 2007/0023512 A1 | 2/2007 | Miller et al. |
| 2008/0059226 A1 | 3/2008 | Melker et al. |
| 2008/0319579 A1 | 12/2008 | Vahlberg et al. |
| 2008/0319789 A1 | 12/2008 | Vahlberg et al. |
| 2008/0319790 A1 | 12/2008 | Vahlberg et al. |
| 2010/0042437 A1 | 2/2010 | Levy et al. |
| 2011/0161108 A1* | 6/2011 | Miller .................. G06Q 10/10 705/3 |
| 2011/0169635 A1* | 7/2011 | Johnson ................ C08L 321/24 340/540 |
| 2012/0203377 A1 | 8/2012 | Paydar et al. |
| 2012/0323362 A1 | 12/2012 | Paydar et al. |
| 2013/0006415 A1 | 1/2013 | Paydar et al. |
| 2013/0006652 A1 | 1/2013 | Vahlberg et al. |
| 2013/0070090 A1 | 3/2013 | Bufalini et al. |
| 2013/0144435 A1 | 6/2013 | Czaplewski et al. |
| 2013/0282392 A1* | 10/2013 | Wurm .................. G06Q 50/22 705/2 |
| 2014/0074284 A1 | 3/2014 | Czaplewski et al. |
| 2014/0138440 A1 | 5/2014 | D'Ambrosio et al. |
| 2015/0170306 A1 | 6/2015 | Harper |
| 2015/0209237 A1 | 7/2015 | Kim et al. |

OTHER PUBLICATIONS

International Patent Application No. PCT/US2016/057298, "International Search Report and Written Opinion" dated Dec. 28, 2016, 15 pages.
PCT/US2016/057298 filed Oct. 17, 2016 received an International Preliminary Report on Patentability dated Apr. 26, 2018, all pages.

* cited by examiner

FIG.7

● 4 Weeks  ○ 12 Weeks  ○ 6 Months  ○ 1 Year  ○ 2 Years — 800

Patient Care Timeline - Oxycodone  804

| Patient SCHEPERLE, ELIZA | | ID 3206128095 | | MRN 920568406 | | | Transactions: 60/360 |
|---|---|---|---|---|---|---|---|
| User | Time/Cabinet | Drug | Issue Amount | Waste/Return | Med Order | Dose Interval | Notable Events | Doses/ 12 Hrs |

| User | Time/Cabinet | Drug | Issue Amount | Waste/Return | Med Order | Dose Interval | Notable Events | Doses/12 Hrs |
|---|---|---|---|---|---|---|---|---|
| KRYSTEN BRUNKE GZ3623 | 9/23/2015 2:55:20 PM HUWC2WRX | OxyCODONE-Acetaminophen (PERCOCET)5-325mg 1Tab | 1 Tab | | 1 Tab, Q4H PRN 102794395 | Start | | 1 |
| SHERLENE LOURDES YJ2830 | 9/24/2015 12:36:32 AM HUWC2WRX | OxyCODONE-Acetaminophen (PERCOCET)5-325mg 1Tab | 2 Tab | | 2 Tab, Q4H PRN 102794396 | (9:41 item) | | 1 |
| SHERLENE LOURDES YJ2830 | 9/24/2015 4:29:12 AM HUWC2WRX | OxyCODONE-Acetaminophen (PERCOCET)5-325mg 1Tab | 2 Tab | | 2 Tab, Q4H PRN 102794396 | 3:53 | | 2 |
| SHERLENE LOURDES YJ2830 | 9/24/2015 4:45:12 AM HUWC2WRX | OxyCODONE-Acetaminophen (PERCOCET)5-325mg 1Tab | | Return 1 Tab | PRN 102794396 | | | 1.5 |
| JOLIE QUISPE MO5893 | 9/25/2015 4:26:49 AM HUWC2WRX | OxyCODONE-Acetaminophen (PERCOCET)5-325mg 1Tab | 2 Tab | | 2 Tab, Q4H PRN 102794396 | 4:29 | | 3 |
| SELENA GIESBRECHT TL5202 | 9/25/2015 8:29:02 AM HUWC2WRX | OxyCODONE-Acetaminophen (PERCOCET)5-325mg 1Tab | 2 Tab | | 2 Tab, Q4H PRN 102794396 | 4:03 | | 3 |
| SELENA GIESBRECHT TL5202 | 9/25/2015 12:06:04 PM HUWC2WRX | OxyCODONE-Acetaminophen (PERCOCET)5-325mg 1Tab | 2 Tab | | 2 Tab, Q4H PRN 102794396 | 3:37 | Discharged Patient | 3 |

FIG. 8

MEDICAL EQUIPMENT WITH DIVERSION MECHANISM

BACKGROUND OF THE INVENTION

Medical facilities, such as hospitals and clinics, often utilize medication dispensing systems, such as carts and/or cabinets to store and dispense medications for use by medical personnel. Due to the high resale value of many medications, medical devices, and other medical supplies, diversion of medical supplies is a major problem at many of these facilities. As many individuals may have access to such medication dispensing systems with little or no supervision, it may be difficult to identify which, if any, individuals may be diverting medical supplies. As such, the prevention of diversion, or change in medical facility protocol may be difficult.

BRIEF SUMMARY OF THE INVENTION

Embodiments of the present invention provide systems and methods for identifying possible diverters of medications and/or other medical supplies by analyzing users' usages of medication dispensing systems. Possible diverters may be flagged and/or prevented from accessing the medication dispensing systems. This provides a medical facility an opportunity to investigate any flagged users to evaluate whether the users' behavior amounts to diversion and/or is indicative of a need for a protocol change.

In one aspect, a medication dispensing system for identifying medical diverters is provided. The system may include an interior where items are stored, a door providing access to the interior, and a locking mechanism configured to lock the door in a closed position. In the closed position the door may prevent access to the interior. The system may also include a computing device having a memory and a processor. The processor may be configured to identify a user pool. The user pool may include a plurality of users having similar job performance functions. The processor may also be configured to retrieve use data for each of the plurality of users from the medication dispensing system. The use data may be indicative of when each user accesses the medication dispensing system. The processor may be further configured to analyze the use data to identify periods of use of the medication dispensing system for each user within the user pool. The processor may be configured to determine boundaries of work shifts based on the periods of use and to organize the user pool into work shifts. Each work shift may define a contiguous period of time that a particular user of the plurality of users worked. The processor may also be configured to determine a comparison period including a time period within which users of the user pool may be compared and to identify diversion data for each user within the comparison period. The diversion data may be indicative of behavior associated with diversion of one of a plurality of particular forms of at least one medication type. The processor may be further configured to generate a diversion score for each of the plurality of particular forms of the at least one medication type by averaging the diversion data per number of work shifts worked for each user during the comparison period and statistically comparing the averaged diversion data for the plurality of users to calculate the diversion score. The diversion score may be indicative of a likelihood that a particular user is diverting a particular one of the plurality of the at least one medication type. The processor may be configured to combine the diversion scores for each of the plurality of particular forms of the at least one medication type for a single user within the comparison period to generate a group score for the single user. The group score may be associated with the at least one medication type. The processor may be configured to determine a consistency factor for the group score. The consistency factor may indicate a consistency over time of the single user having a group score that exceeds a group threshold. The processor may be configured to generate an overall diversion score based at least in part on the group scores for each of the at least one medication type, consistency factors for each group score, and a diversion profile of the at least one medication type. The processor may also be configured to determine whether any user's overall score exceeds an overall threshold and to flag any user whose diversion score exceeds the overall threshold as a possible diverter. The processor may be further configured to lock any flagged users out of the medication dispensing system such that the any flagged users do not have access to the interior.

In another aspect, a method for identifying medical diverters is provided. The method may include identifying a user pool. The user pool may include a plurality of users having similar job performance functions. The method may also include retrieving use data for each of the plurality of users from a medication dispensing system. The use data may be indicative of when each user accesses the medication dispensing system. The method may further include analyzing the use data to identify periods of use of the medication dispensing system for each user within the user pool. The method may include determining boundaries of work shifts based on the periods of use and organizing the user pool into work shifts. Each work shift may define a period of time that a particular user of the plurality of users worked. The method may also include determining a comparison period including a time period within which users of the user pool may be compared and identifying diversion data for each user within the comparison period. The diversion data may be indicative of behavior associated with diversion of one of a plurality of particular forms of at least one medication type. The method may further include generating a diversion score for each of the plurality of particular forms of the at least one medication type by averaging the diversion data per number of shifts worked for each user within the work shift during the comparison period and statistically comparing the averaged diversion data for the plurality of users to calculate the diversion score. The diversion score may be indicative of a likelihood that a particular user is diverting a particular one of the plurality of the at least one medication type. The method may include combining the diversion scores for each of the plurality of particular forms of the at least one medication type for a single user within the comparison period to generate a group score for the single user. The group score may be associated with the at least one medication type. The method may include determining a consistency factor for the group score. The consistency factor may indicate a consistency over time of the single user having a group score that exceeds a group threshold. The method may also include generating an overall diversion score based at least in part on the group scores for each of the at least one medication type, consistency factors for each group score, and a diversion profile of the at least one medication type. The method may also include determining whether any user's overall score exceeds an overall threshold and flagging any user whose overall score exceeds the overall threshold as a possible diverter.

BRIEF DESCRIPTION OF THE DRAWINGS

The present invention is described in conjunction with the appended figures:

FIG. 7 is a dashboard for viewing group scores for various drugs of a selected user.

FIG. 8 is a dashboard for viewing interactions with a particular medication type for a selected user.

DETAILED DESCRIPTION OF THE INVENTION

Figure 1:
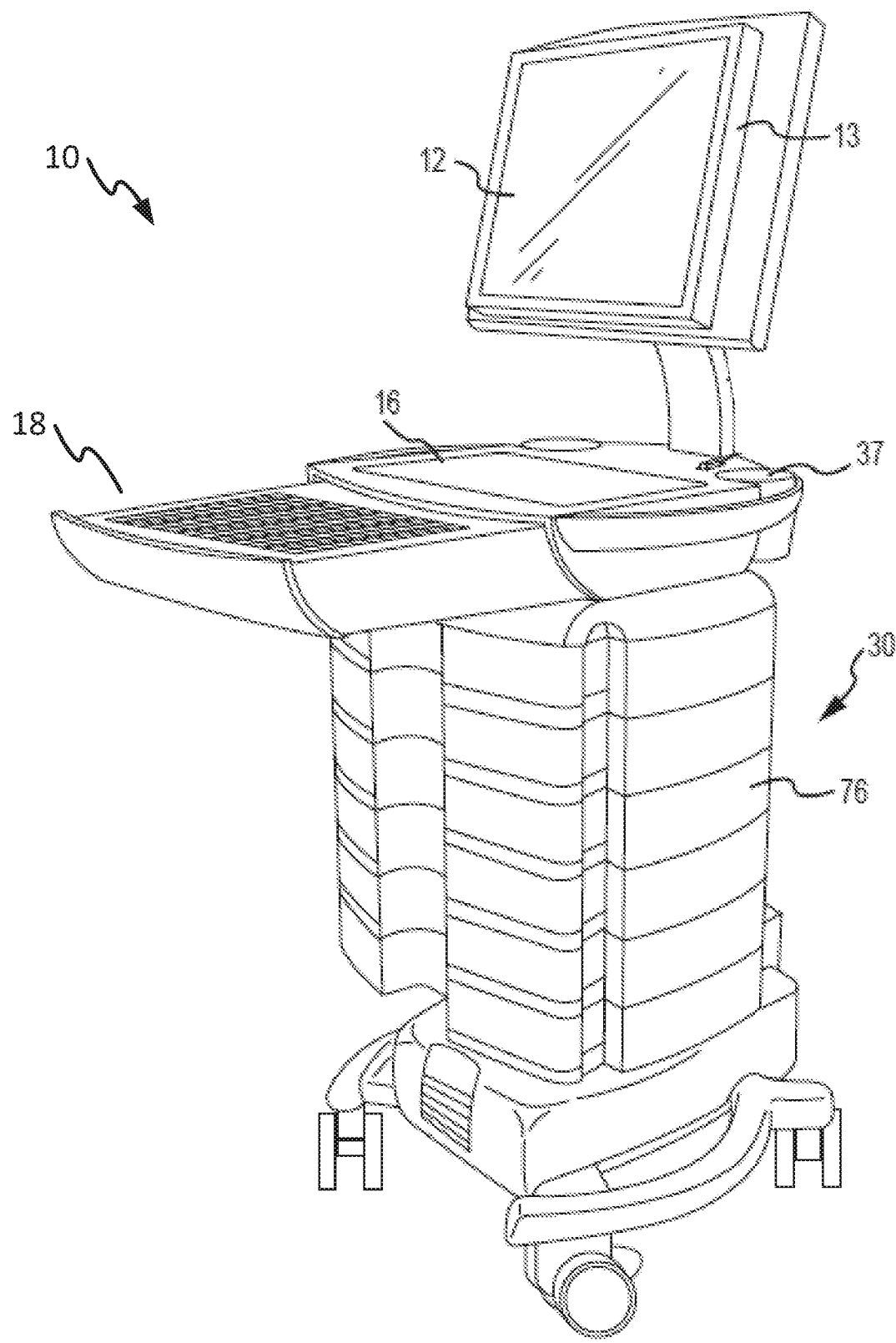
FIG. 1 is a structure diagram of a medication dispensing cart according to embodiments.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It will be understood that various changes may be made in the function and arrangement of elements without departing from the spirit and scope of the invention as set forth in the appended claims. Merely by way of example, any embodiment described herein may or may not have any of the features discussed therewith, and may or may not have any feature discussed with respect to other embodiments.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Embodiments of the present invention provide systems and methods for identifying possible diverters of medications and/or other medical supplies by analyzing users' usages of medication dispensing systems. Each user's actions may be compared to those of other users to identify statistically anomalous behavior. Medication dispensing systems may include carts, cabinets, and/or other systems that provide controlled access to medications, medical devices, and/or other medical supplies. These systems may log information, or use data, related to users' access of the systems. For example, information may include a type and/or quantity of a medication, a device, and/or supply that a user withdrew from the system. The information may also include a timestamp and/or records of returning the supply to the system, disposal of a portion of the supply, dosage amounts, and/or other records related to the dispensing and/or administration of a medication or other medical supply.

Oftentimes, a work schedule for the users of a medical facility may not be available. In such cases, to compare similar users, predicted or approximate work shifts must be determined. Typically, users, such as nurses, work in blocks of time, such as 12-hour shifts, with one shift being days (e.g., 6 am-6 pm or 7 am-7 pm) and a second shift being nights (e.g., 6 pm-6 am or 7 pm-7 am). Each user's uses, and gaps between uses, of the medication dispensing systems may be monitored and analyzed to generate a predicted work schedule that matches, or closely matches, the actual work schedule for each of the users. Diversion data may be identified that is indicative of a behavior associated with diversion. This data may be a subset of the use data from the medication dispensing systems or may be provided from other sources. Diversion data may include any data related to behavior inconsistent with proper handling and/or issuance of a medication or other medical supply. In some embodiments, use data may be compared with other data, such as medical orders (i.e., prescriptions) patient charts, and/or other medical records to identify discrepancies that may qualify as diversion data.

Diversion data may be used to generate a diversion score. For example, the diversion data may be in terms of a number of instances of possible diversion. The number of instances may be averaged over a number of shifts worked to arrive at the diversion score. In other embodiments, each type of diversion may have a value associated with it. The value may be indicative of a likeliness of diversion associated with a particular action. Diversion scores may represent averages such that individual users may be compared to the pool of users, such as by comparing the users' diversion scores to a baseline diversion score. The baseline score may be generated by averaging diversion scores for all users within a work shift or other similar group. This allows users whose potential diversion actions are outliers of the pool to be identified. Some diversion data is likely to exist for all users, and by comparing each user to the baseline score, only diversion behavior above a normal amount or range of amounts of diversion related behavior will be singled out. For example, users whose diversion score exceed the baseline score, or exceed the baseline score by a particular amount or threshold, may be flagged as a possible diverter. In some embodiments, possible diverters may be prevented from accessing the medication dispensing systems. This provides a medical facility an opportunity to investigate any flagged users to evaluate whether the users' behavior amounts to diversion and/or is indicative of a need for a protocol change. In cases where the baseline score is excessively high, the facility may need to address general operating protocol to identify possible reasons for the consistently high diversion scores.

Referring now to the figures, FIG. 1 illustrates a medication dispensing cart 10 (e.g., a Mobile Medication System (MMS) cart) that includes a computer/monitor 12 (also referred to herein as touch screen 12), preferably an all-in-one unit having the computing device positioned within a housing behind the display monitor 12, although other configurations (e.g., separate computing devices and monitors) could be used. In some embodiments, computer monitor 12 is a touch screen display that allows a caregiver or other user to interface with the computing device and input information thereto by selecting one or more menus, inputting information, and the like via contacting monitor 12 with a finger or input device. Medication cart 10 also includes a work surface 16, which may include a slide out keyboard 18. Keyboard 18's keypad provides a second information input mechanism so that various information, such as entry of security access codes, patient related information, and the like may be input into the system. For example, medication information, caregiver ID, doses, patient information, time, date, and the like may be input into the computing system as treatments and/or medications are administered to the patient.

Work surface 16 is mounted atop a base, such as a rolling base. Work surface 16 can optionally include holders 37 for storing items, such as antibacterial lotions, medical supplies (gloves, and the like), writing instruments, writing pads, drinks, and the like which the caregiver or user may need when administering care with medication cart 10. Medication dispensing cart 10 may include other peripheral devices, such as a barcode scanner (not shown), mouse (not shown), etc. The keyboard 18, barcode scanner, mouse, and/or other devices may be sealed to prevent the spread of infectious diseases. Medication cart 10 and/or work surface 16 may be configurable so that additional peripheral device may be connected to medication cart 10, such as a vital life sign monitor, scanner, etc.

Touch screen 12 may include a ground guard 13 to reduce or eliminate electrostatic discharge, which may shock a user of the cart 10 or damage sensitive equipment, such as the computer system or touch screen controller. Ground guard 13 may discharge electrostatic charges generated as the caregiver/user performs various duties, such as administering treatment or medications to patient located within a facility. Ground guard 13 may be positioned around an outer periphery of touch screen 12 to dissipate such charges. In some embodiments, ground guard 13 comprises a metal frame (e.g., metal strip and/or gasket) around the periphery of touch screen 12. The metal frame may be electrically grounded to medication cart 10 (e.g., an electrically conductive chassis of medication cart 10) so that electric charges are dissipated as the caregiver/user touches and interacts with monitor 12.

As described below, cassette 76 may be coupled or stacked with other cassettes to form a cassette stack 30 (also referred to herein as cassette system 30). Backplane 27 may also be electronically coupled with a cassette controller unit (not shown) that controls or interfaces with the one or more plurality of cassettes 76 of cassette stack/system 30 to provide the various access controls and/or features described herein. A backplane (not shown) may house the cassette controller for monitoring the status and activities of cassettes 76 and/or receiving input for touch screen 12. In other embodiments, the cassette controller may be a separate unit apart from the backplane.

Some of the features that may be provided by the cassette controller and/or backplane include: controlling the locking and unlocking of each of the bins of the individual cassettes, detecting the open/close condition of the individual bins, detecting the lock/unlock condition of the individual bins locking mechanism, automatically detecting the cassette type and configuration (e.g., detecting whether the cassette 76 is a roughly 3 inch or 6 inch cassette), automatically detecting the presence of a cassette 76 electronically coupled with (i.e., plugged into) a port (not shown), controlling guiding lights (not shown), charging of a backup battery (not shown), switching the power source between the main power source (i.e., lithium ion battery, external power source, etc.) and the backup battery, controlling an alarm mechanism (not shown), interfacing with other components of the cart 10 and/or other components of other systems (e.g., central administrator), and the like.

The cassette controller and/or backplane may include a storage medium (e.g., non-volatile memory, EEPROM, etc.) so that the conditions of the cart 10 and/or cassettes 76 may be monitored and recorded. For example, the cassette controller and/or backplane 27 may record and/or store information about the opening/closing of the bins, alarm conditions such as when unauthorized bin access occurs, power loss and recovery of the cart 10 occurs, and the like. This history can be provided to a central administrator, such as a central administrator 400 shown in FIG. 4, so that the real time condition of the cart 10 and/or the history of the cart 10 can be monitored.

The cassette controller and/or backplane may monitor the status of cart 10 and/or cassettes 76. For example, the cassette controller and/or backplane may be electronically coupled with one or more sensors (not shown) to determine if the lock mechanism is locked or unlocked, if the door is open or closed, etc. In one embodiment, the sensors respond to requests/communications received from the cassette controller and/or backplane. In another embodiment, the sensors provide information without receiving requests from the cassette controller, such as when the sensors sense a bin is opened and/or a locking mechanism is disengaged, etc.

For example, the cassette controller and/or backplane may receive an input from a caregiver or other user to unlock one of the cassettes 76 that includes a patient's medications. The cassette controller and/or backplane may instruct a locking mechanism, such as a solenoid, to unlock the requested cassette 76 and/or bin. To ensure that the locking mechanism has actually unlocked the requested cassette 76 and/or bin and that an error/failure has not occurred, the cassette controller and/or backplane may be coupled with a sensor (e.g., photointerrupter sensor, etc.) and feedback loop and the status of the locking mechanism may be determined, such as if the solenoid has been disengaged. Likewise, a sensor may be used to determine if the bin door is opened or closed. In this manner, the actual status of the locking mechanism and/or bin may be determined to ensure that the actual status corresponds with what the cart's control system (and/or central administrator) believes the status to be (e.g., verifying that the bin is actually closed). The status of the locking mechanism and/or bin may be checked intermittently (e.g., at specified or irregular time intervals) or continuously. If the status of the bin is other than that expected by the cart's control system (e.g., the locking mechanism is unlocked when the control system indicates the locking mechanism as being locked), the cart's control system may be updated, the discrepancy recorded, an alarm triggered, and/or a control system (e.g., central administrator) alerted to notify one or more individuals or systems about the discrepancy. Likewise, the history of any discrepancies can be stored so that the individual carts and/or the entire cart system can be monitored and problems addressed.

Figure 2:
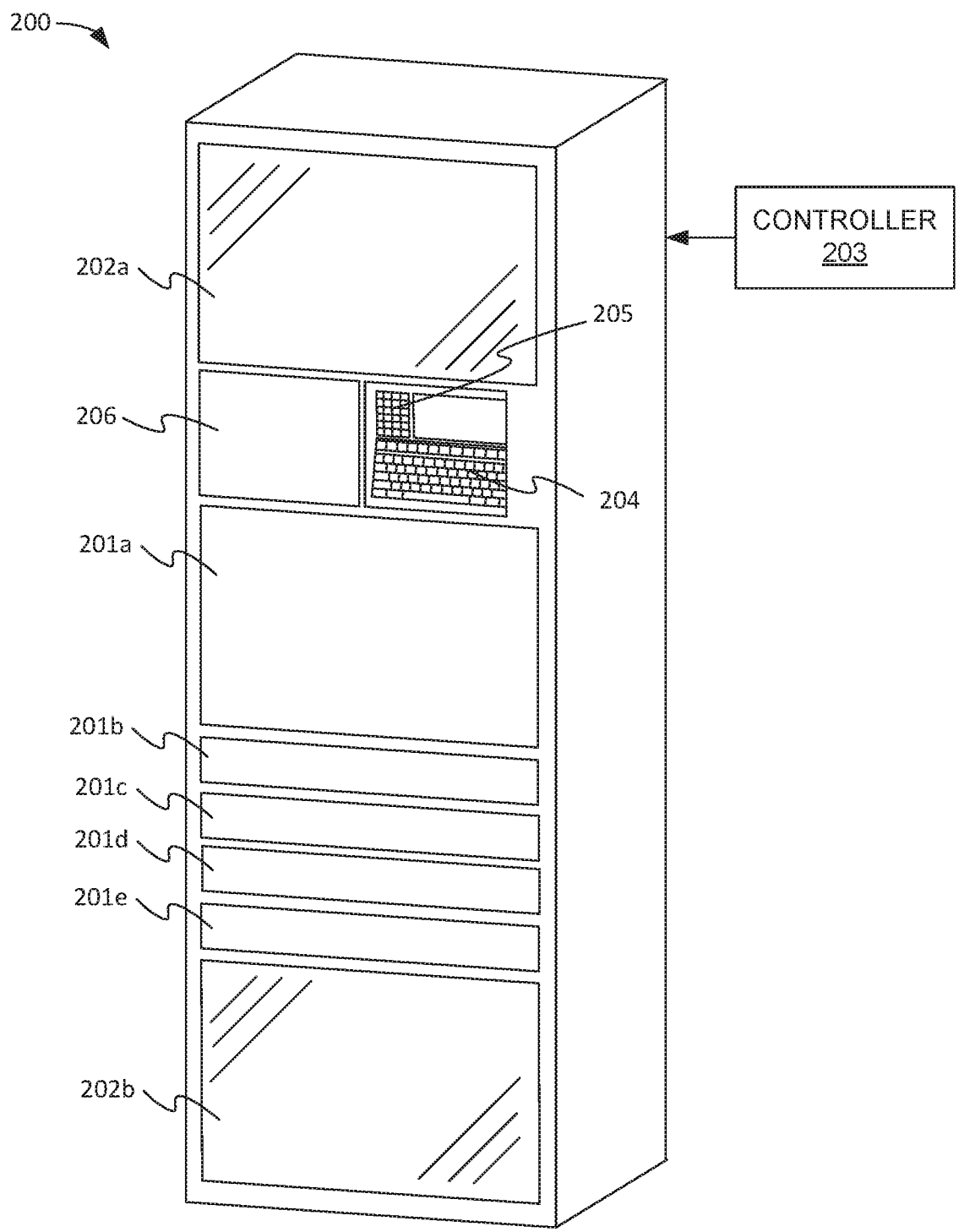
FIG. 2 is a structure diagram of a medication dispensing cabinet according to embodiments.

FIG. 2 illustrates a medication dispensing cabinet 200, in accordance with embodiments. Cabinet 200 includes a plurality of compartments, including drawers 201a-201e, and compartments accessible through doors 202a and 202b. Medication dispensing cabinet 100 also includes a controller 203, and one or more data entry devices such as keyboard 204 and keypad 205. A display 206 enables communication of information to a user of medicine dispensing cabinet 200. In some embodiments, a medication dispensing cabinet may include other devices as discussed in more detail below.

Controller 203 may include a computer, which further includes a processor, memory, input/output interfaces, and other components. Controller 203 may communicate remotely with other computerized systems, such as medical records systems, inventory and accounting systems, and the like.

The various storage compartments such as drawers 201a-201e may be under the control of controller 203. For example, each of drawers 201a-201e may include an electronically controllable locking mechanism, and may only be openable under the control of controller 203. In addition, controller 203 may store information about what supplies are stored in which compartments of medication storage cabinet 200. In one typical basic usage scenario, a health care worker may enter, using keyboard 204 or another input device, an identification of a patient who is under the care of the health care worker, and who will need medication during the worker's current rounds. Controller 203 may access the patient's medical file and determine what medications have been prescribed for that patient. Controller 203 may then open only the drawer or drawers containing the prescribed medications for the patient. A particular compartment within the correct drawer may be highlighted, for example with a lighted indicator, to draw the health care worker to the correct medication. The health care worker can then remove the patient's prescribed medication. The level of control exercised by controller 203 may help in preventing medication and dosing errors, by reducing the likelihood that a health care worker will remove an incorrect medication from medication dispensing cabinet 200. In addition, controller 203 may document and record which medication was dispensed, and may forward that information to inventory and accounting systems.

Many other features and functions are possible as well. For example, the health care worker may enter his or her identification as well, and controller 203 may provide access only to those medications and supplies for which the worker is authorized to access.

While medication dispensing cabinet 200 is shown as a stationary device, the invention is not so limited. Cabinets according to other embodiments may be portable, for example to facilitate transporting medications and supplies from a central supply store to a particular ward or department of a facility. It will be recognized that the particular arrangement of drawers, doors, or other features of a cabinet according to embodiments of the invention may be varied. For example, some cabinets or dispensing carts embodying the invention may use only drawers, only doors, or utilize some other access method. Compartments within drawers may also be individually lockable and controllable. Additional types of dispensing units are described in the following commonly owned U.S. Patents and patent applications, the contents of which are hereby incorporated by reference: U.S. Pat. No. 6,272,394, issued on Aug. 7, 2001 to Lipps, U.S. Pat. No. 6,385,505, issued on May 7, 2002 to Lipps, U.S. Pat. No. 6,760,643, issued on Jul. 6, 2004 to Lipps, U.S. Pat. No. 5,805,455, issued on Sep. 8, 1998 to Lipps, U.S. Pat. No. 6,609,047, issued on Aug. 19, 2003 to Lipps, U.S. Pat. No. 5,805,456, issued on Sep. 8, 1998 to Higham et al, U.S. Pat. No. 5,745,366, issued on Apr. 28, 1998 to Higham et al., an U.S. Pat. No. 5,905,653, issued on May 18, 1999 to Higham et al., U.S. Pat. No. 5,927,540, issued on Jul. 27, 1999 to Godlewski, U.S. Pat. No. 6,039,467, issued on Mar. 21, 2000 to Holmes, U.S. Pat. No. 6,640,159, issued on Oct. 28, 2003 to Holmes et al., U.S. Pat. No. 6,151,536, issued on Nov. 21, 2000 to Arnold et al., U.S. Pat. No. 5,377,864, issued on Jan. 3, 1995 to Blechl et al., U.S. Pat. No. 5,190,185, issued on 5 Mar. 2, 1993 to Blechl, U.S. Pat. No. 6,975,922, issued on Dec. 13, 2005 to Duncan et al., U.S. Pat. No. 7,571,024, issued on Aug. 4, 2009 to Duncan et al., U.S. Pat. No. 7,835,819, issued on Nov. 16, 2010 to Duncan et al., U.S. Pat. No. 6,011,999, issued on Jan. 4, 2000 to Holmes, U.S. Pat. No. 7,348,884, issued on Mar. 25, 2008 to Higham, U.S. Pat. No. 7,675,421, issued on Mar. 9, 2010 to Higham, U.S. Pat. No. 6,170,929, issued on Jan. 9, 2001 to Wilson et al., U.S. Patent Application Publication No. 2008/0319579 of Vahlberg et al., published on Dec. 25, 2008, U.S. Patent Application Publication No. 2010/0042437 of Levy et al., published on Feb. 18, 2010, U.S. Patent Application Publication No. 2012/0203377 of Paydar et al., published on Aug. 9, 2012, and U.S. Patent Application Publication No. 20130006415 of Paydar et al., published on Jan. 3, 2013.

In one aspect, a medication dispensing cabinet may provide multiple integrated printers. The different printers may provide different functions that require different media or other characteristics. For example, it may be desirable to provide a printed receipt each time a health care worker removes medication or supplies from cabinet 200. Such a receipt may be placed in a patient's file, or attached to a treatment order. It may also be desirable in some applications to print an adhesive label that describes a particular medication or instructions for use of a particular medication. Such a label may be adhered to a syringe, bottle, or other container into which the medication is transferred. As such, a label printer requires a different kind of media than the receipt printer. Printers may also be used to print hard copy versions of reports and graphs, such as diversion reports.

Medication dispensing systems, such as cart 10 and cabinet 200, may include additional functionalities beyond controlling access to medications and other medical supplies. For example, individual storage compartments may be temperature controlled. The systems may also include sensors, such as RFID sensors that may automatically detect and track removal and/or replacement of items within a medication dispensing system. Tracking systems enable a quick, accurate assessment of inventory that may also monitor which users took medical supplies. Some of this tracking information may be identified as diversion data. Such tracking systems are described in, for example, U.S. Pat. No. 7,348,884, the entire contents of which is hereby incorporated by reference.

The medication dispensing systems described herein may monitor user interactions and identify possible diversion behavior in the form of diversion data. The medication systems may track this diversion data and produce reports or other indications that a user may be a possible diverter. Such monitoring may be done using a computing device of the medication dispensing system. For example, the cassette controller and/or backplane of cart 10 and/or controller 203 of cabinet 200 may perform such functions. As one example, a medication dispensing system may log information related to users' access of the systems and store the information as use data. For example, the use data may include a type and/or quantity of a medication issued and/or a device and/or supply that a user withdrew from the system. The information may also include a timestamp and/or records of returning the supply to the system, records of disposal of a portion of the supply, records of administered dosage amounts, and/or other records related to the dispensing and/or administration of a medication or other medical supply. This data, along with data from other sources, may be identified as diversion data that may be used to determine which users are possible diverters.

Figure 3:
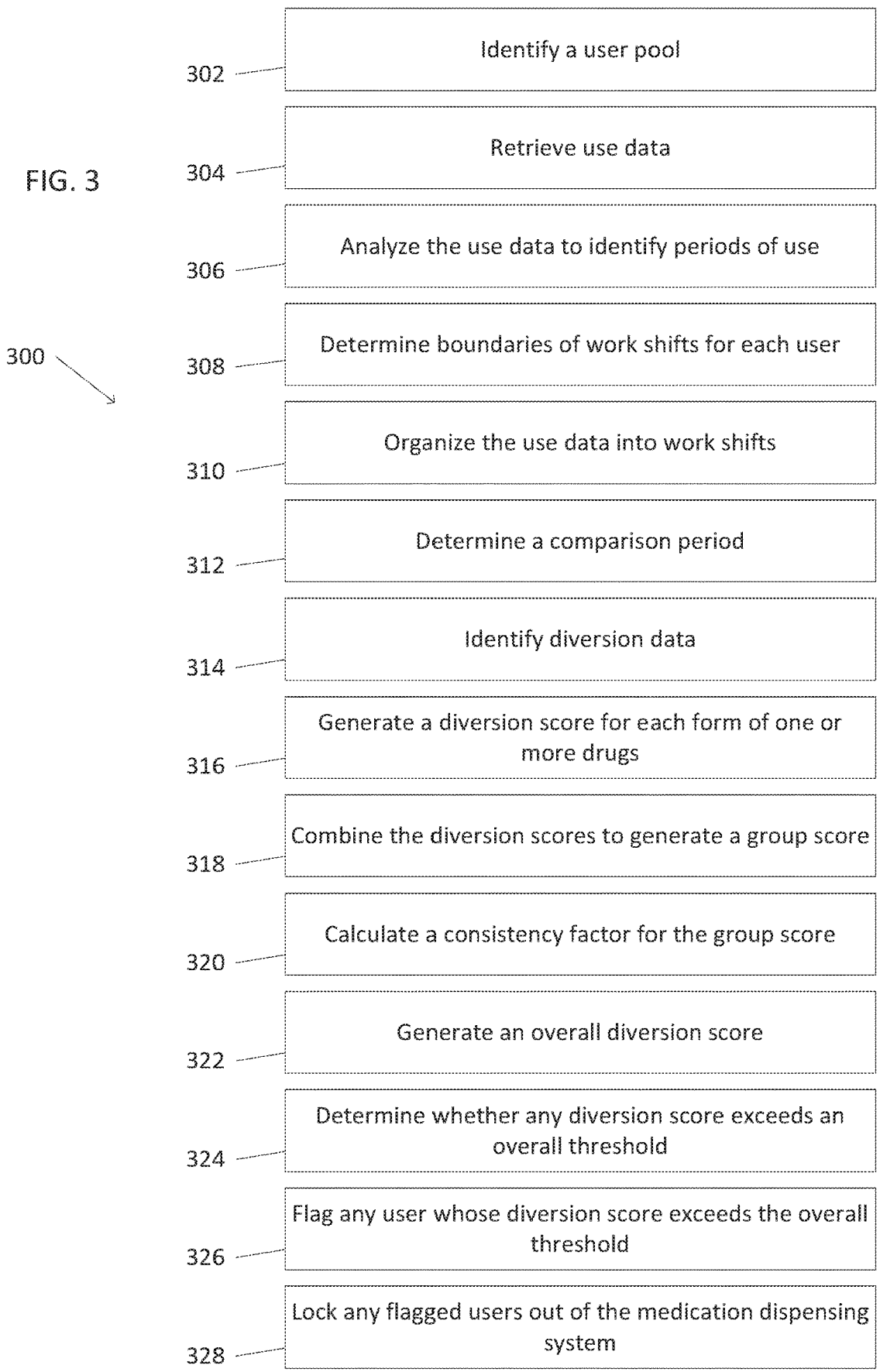
FIG. 3 is a flowchart of a method of identifying possible diverters using a medication dispensing system according to embodiments.

FIG. 3 depicts a flowchart of a process 300 that may be executed by a computing device of a medication dispensing system, such as those described above. For example, the medication dispensing system may include an interior where items are stored, a door providing access to the interior, and a locking mechanism configured to lock the door in a closed position. In the closed position the door may prevent access to the interior. The medication dispensing system may also include a computing device, such as a cassette controller or controller 203 as described above, having a memory and a processor. The processor may be configured to identify a user pool at block 302. The user pool may include a number of users having similar job performance functions. For example, user pools may include nurses, pharmacy technicians, anesthesiologists, and/or other medical practitioners. Oftentimes, the user pool will include only those medical practitioners that have access to items within the medication dispensing system. The user pool may be predetermined, such as a group of all nurses that have access to the medication dispensing system, or may be user-defined such that an administrator may select a particular subset of users to evaluate.

The processor may also be configured to retrieve use data for each of the users at block 304. The use data may be indicative of when each user accesses the medication dispensing system. As noted above, use data may include type and/or quantity of a medication issued, a device and/or supply that a user withdrew from the system, a timestamp, records of returning the supply to the system, records of disposal of a portion of the supply, records of administered dosage amounts, and/or other records related to the dispensing and/or administration of a medication or other medical supply. The processor may be further configured to analyze the use data to identify periods of use of the medication dispensing system for each user within the user pool at block 306. For example, the medication dispensing system may monitor timestamps of each use of the medication dispensing system to determine likely periods of work or activity for each user. In some embodiments, gaps between uses of the medication dispensing system may be identified as well. At block 308, the processor may be configured to determine boundaries of work shifts for the user pool and to organize the use data into work shifts at block 310. For example, a first user may access the medication dispensing system several times between 7 am and 5 pm, a second user may access the medication dispensing system between 7:30 am and 6:30 pm, and third user may access the medication dispensing system between 7 pm and 6:30 am. The medication dispensing system may determine that each of the time spans represented a single shift of work for each of the users. The system may further determine that the first and the second user worked a day shift, and that the third user worked a night shift. This enables a comparison of similar users, who are operating under similar facility conditions, on similar patients, and/or under similar supervision. It also enables the normalization of the usage and noncompliance events per shift so that user to user comparisons yield valid measures when looking at longer time periods like weeks or months. In some embodiments, an actual schedule may be available to determine shifts. In such cases, the actual schedule may be input and/or received from an outside source, rather than using use data to approximate a schedule. It will be appreciated that shifts represent periods of activity for users, and may or may not correspond completely with actual worked shifts. In some embodiments, the identified gaps may also be useful in determining the boundaries of worked shifts.

The processor may also be configured to determine a comparison period including a time period within which users may be compared at block 312. For example, a comparison period ranging from a single shift, to shifts over a period of weeks or months may be selected. This allows for analysis of short term issues and identification of more ongoing diversion behavior. Additionally, by having a comparison range of several weeks or more, more statistically valid determinations are possible. For example, a comparison period of a single work shift may include atypical behavior due to a number of factors such as high or low patient load, over or under staffing, patients requiring an abnormal amount of attention, and/or other factors. Longer comparison periods may serve to provide a picture of normal operating conditions.

The processor may be configured to identify diversion data for each user within the comparison period at block 314. The diversion data may be indicative of behavior associated with diversion, such as the diversion of one particular form of one or more medication types. For example, the diversion data may relate to a 5 mg oxycodone pill, with other dosages and/or drug delivery forms of oxycodone tracked separately. Additionally, it will be appreciated that a medication type may be used to reference a single drug and/or a family of drugs. Typically, the diversion data relates to a use of medications and/or other medical supplies in a manner that is not in accordance with normal medical procedure. In some embodiments, the diversion data may be generated from the use data. For example, abnormal amounts of medication issued, high frequencies of issuing medication, inventory counts being abnormal, and/or other activity included in the use data may be identified as diversion data. In some embodiments, additional data may be retrieved and identified as diversion data. For example, medical orders identifying a type, schedule, and/or dosage of medication may be used to identify diversion data. Additionally, or alternatively, medical charts with records of what symptoms, diagnoses, allergies, and/or medications are relevant to a patient and/or other records or information may be received by the medication dispensing system. Such additional information may be received from manual input by an issuing nurse or other medical personnel, from a central records entry, such as when records of medical charts are entered into a facility's records system, from a pharmacy records system, and/or from other sources. This additional information, either alone, or when compared to use data, may be used to identify diversion data.

As one example, the medication dispensing system may receive a number of medical orders relating to medications issued from the medication dispensing system. The medication dispensing system may then analyze medications ordered from the medical orders against the actual issuance of medications from the medication dispensing system to identify instances of issuance of medications that were inconsistent with medical orders, such as by incorrect doses, timing, patients, type of medication, and the like. As another example, an amount of a particular drug dispensed from the medication dispensing system may be compared with medical documentation, such as a patient chart, to identify diversion data. Here, the diversion data would include discrepancies between the amount dispensed and the medical documentation.

There are multiple mechanisms of diversion used by diverters, and each of these mechanisms may have multiple data indicators that can be tracked to detect diversion. Other examples of diversion data include a number of instances an issuance of medication was inconsistent with a medical order, a number of instances a medication was issued to a patient who should have been discharged, a number of times a high amount or excessive amount of a medication was issued, a number of times a medication was issued too early, a number of times a drug was issued at a high end of an acceptable range or beyond, a number of cancellations of medication withdrawals with detection of a bin being opened, a number of times a medication was issued off schedule from a medical order, and/or any other behavior that is inconsistent with normal and/or proper facility and/or medical procedure. Manual records may include records of replacement and/or waste, based on a patient not requiring a full dose. Inventory and uses may be checked against medical records and entries to identify whether such replacement or waste constitutes possible diversion. While diversion data may be noted as a number of instances, it will be appreciated that other data forms may be used. For example, a severity or likeliness of a particular action indicating diversion may cause the action to be assigned a diversion value accordingly. Thus, behavior highly tied to diversion may have a high score, such as 10, while less likely diversion behavior may have an assigned score of 2. These values may be predetermined and/or assigned by a facility based on behaviors with which the facility is most concerned. In some embodiments, the values may vary for similar actions, such as assigning higher scores for high waste amounts than low waste amount or for more valuable medications than for inexpensive medications.

Oftentimes, diversion data may only be tracked for some or all controlled substances, but any substance and/or supply within a medication dispensing system may be monitored. Medications at higher risks for diversion may also be monitored while lower risk medications are not tracked. For example, high cost and/or supplementary/secondary medications may be monitored as well. Additionally, each form of a particular medication may have its own diversion data. For example, a user's issuance of morphine in pill form may be tracked separately from issuance of morphine in injectable form. In other embodiments, diversion data may be tracked for each medication, with all forms of the medication being covered under the same data.

The processor may be further configured to generate a diversion score for each form of each of the medications at block 316. For example, the medication dispensing system may aggregate the diversion data for a particular item and user and average the diversion data by the number of shifts worked by the user within the comparison period. The processor may then evaluate whether a user's averaged diversion data is statistically anomalous compared to the rest of the users with similar types of shifts in the comparison period, such as by using quartile statistics, to establish a diversion score. The diversion score may be indicative of a likelihood that a particular user is diverting medication. For example, a user may have 28 instances of diversion behavior within a comparison period spanning 8 shifts. The user's average diversion data may be 3.5, representing an average of 3.5 instances indicative of diversion per shift. As one example, when compared to other users' average diversion data for the same comparison period with similar shifts, the user may be found to have data which is 3 inter quartile ranges above the third quartile, and this may be used as a basis for the diversion score. Other types of diversion scores may be generated in a similar manner. For example, where diversion data is assigned a diversion value based on the likelihood that a given behavior indicates diversion, the diversion values may be added up and averaged over the number of shifts worked, and then compared to other users to generate a score. In some embodiments, a diversion score may represent a likelihood of diversion for only a single indicator of diversion for a single medication or form of a single medication. If each diversion indicator form has its own diversion score, a combined diversion score for the single medication form as a whole may be generated by aggregating the diversion data and/or diversion scores for each form of the medication.

At block 318, the processor may be configured to combine all of the diversion scores within the comparison period for all forms of a single medication and combine them into a single group score for that medication as a whole. In another embodiment, the processor may be configured to collect all of the diversion scores for a single diversion mechanism for all forms of a single medication. The diversion scores may be combined into a single score for that diversion indicator for that medication as a whole within that comparison period. The different scores for the indicators may be further combined into a single group score for this medication as a whole.

At block 320, the processor may be configured to calculate a consistency score indicating how consistently over time a user has had a diversion score which is statistically significant for an overall medication, individual form, and/or diversion indicator for a single form. As one example, a user may have weekly scores of 3 for the first week, followed by 1, 2, 5, and 6. These weekly scores may yield a single consistency score of 2.5 to represent the number of weeks their score has been statistically significant, or otherwise exceeding a group threshold.

At block 322, the processor may be configured to collect all of the diversion and consistency scores across all medications for a single user and combine them, along with data from a diversion profile, to generate a single overall score for the user. This overall score may combine the individual medication scores, taking into consideration knowledge derived from experts in the field on how likely each medication is to be diverted, and whether the medication itself has the potential for abuse or whether the medication is a supplementary medication that is used to substitute for an abused medication or cover the symptoms of an abused medication. Further, this overall score may be generated in such a way that it maintains its relevance as a normalized score even though it may not be combined with a statistical formula. The diversion profile may include data for classifying various forms and/or dosages of medication into medication types. The diversion profile may also provide information indicating the likelihood that each particular form and/or type of medication is to be diverted. Based on this information, a weighting of each of the diversion factors may be individually generated for each medication type. Such information may be available both for primary (subject to diversion because the drug is addictive, has a high value and/or is otherwise the primary target of diversion) medications, as well as for secondary (medications used to cover up an addiction). In some embodiments, the diversion profile may be programmed into the medication dispensing system, while in other embodiments, the diversion profile may be provided by a user input and/or from another system. The diversion profile may be a dynamic profile, with the data being updated as more use and diversion data is collected and analyzed, thus making the diversion profile adaptable as a medical facility becomes more knowledgeable and/or sophisticated. It will be appreciated that other forms of generating overall scores may be utilized.

At block 324, the processor may also be configured to determine whether any user's diversion score exceeds the baseline score by a predetermined threshold and to flag any user whose diversion score exceeds the baseline score by the predetermined threshold as a possible diverter at block 326. For example, the threshold may be set to any value above the baseline to flag any above average diversion score, or a minimum amount over the baseline may trigger the flagging. As one example, the medication dispensing system may flag users whose overall score is above 10. Flagged users may be investigated to determine whether the users are actually diverting medications and/or other medical supplies, or whether there is an alternative explanation. In some embodiments, the processor may be further configured to lock any flagged users out of the medication dispensing system such that the flagged users do not have physical access to the interior at block 328. This can prevent further diversion behavior; such as while a user is being investigated. In embodiments where a diversion score is associated with a single medication or a single form of a particular medication, the user may be locked out of only portions of the interior of the medication dispensing system containing the particular medication or form of medication. This allows a medical practitioner to continue performing some or all job functions, while allowing time for an investigation into the possible diversion behavior related to the particular drug or form of drug. The baseline and diversion scores may be tracked over time, such as by generating trend data, which may be used to generate a graphical output of trends of diversion scores and/or baseline scores. Graphical outputs may be printed as hardcopies by the medication dispensing system or other hardware or may be displayed on a screen of the medication dispensing system or other device.

In some embodiments, multiple medication dispensing systems may be utilized in a facility and/or organization. Information from some or all of the medication dispensing systems may be aggregated, such as by a central server or host computer, such that patterns of diversion and/or best practices among different medication dispensing systems and/or facilities may be monitored. This allows for the identification of especially bad diverters system-wide, and/or the evaluation of what protocols and/or facility practices may be working more effectively than others. For example, if a system of five facilities indicates that a first facility has a very low baseline diversion score compared to the other four facilities and a second facility has a very high baseline diversion score compared to the other four facilities, an administrator may be able to look at differences in facility protocols to identify which may need to be changed from the abnormally high facility to achieve a lower baseline diversion score. Using such information, administrators may be able to identify situations that lend themselves to diversion such that adjustments may be made to tighten up the procedures. This may result in lower baseline scores, as well as prevent individual users from exhibiting diversion behaviors.

Upon generation of the overall diversion scores for each user, a trend chart may be generated that includes a history of overall diversion scores for each of the flagged users. Each of the trend charts may be displayed on a remote device, such as a smartphone, laptop, and/or other computing device. An input may be received from the remote device, such as a user of the remote device clicking or otherwise interacting with an icon or other portion of a display of the user device associated with one of the flagged users. A group score trend chart may then be generated that includes a history of the group score for the one of the flagged users, which may then be displayed on the remote device. Further interaction with a group score icon on the remote device may cause a usage chart for the particular type of medication associated with the group score to be shown.

Figure 4:
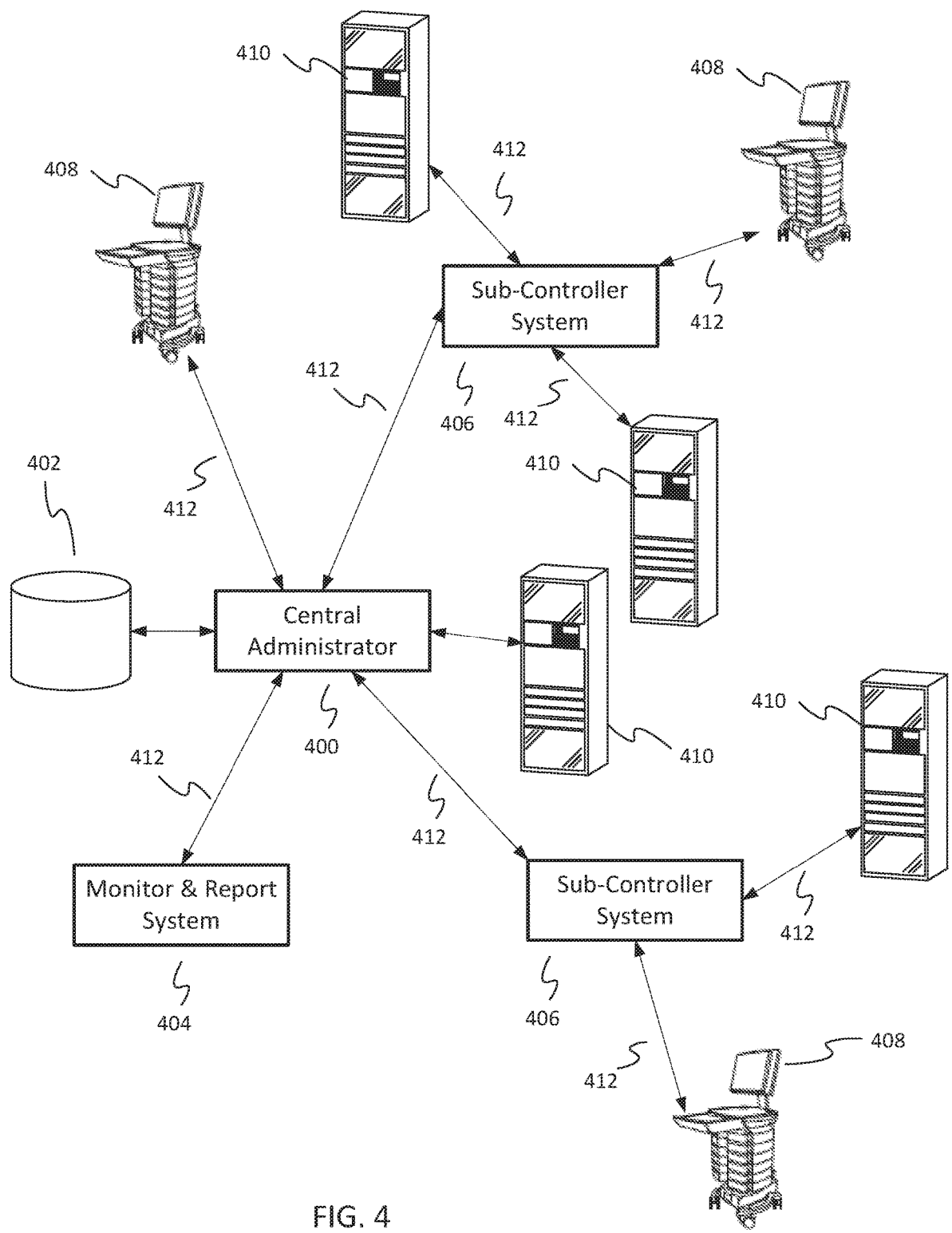
FIG. 4 is a system diagram of a network of medication dispensing systems according to embodiments.

Illustrated in FIG. 4 is a simplified system of a central administrator 400 that may centrally manage a number of medication dispensing systems, such as medication carts 408 and medication cabinets 410. Medication carts 408 and medication cabinets may be similar to cart 10 and medication dispensing cart, respectively, as described herein. Central administrator 400 may be tied to a hospitals Admission Discharge Transfer (ADT) system, Pharmacy Information System (PIS), administration system, and/or Automated Dispensing Machine (ADM). Further, the central administrator 400 may be a sub-component of the ADT/ADM system or may be a separate cart 408 and/or cabinet 410. Each of the medication carts 408 and/or cabinet 410 may include a power system controller, cassette controller, and computer/monitor controller as described above, which monitors information about various aspects of the cart 408 and/or cabinet 410 (e.g., user access, cassette/bin access, battery status, patient information, unauthorized access, use data, diversion data, etc.). This information may be provided to the central administrator 400 so that the central administrator 400 can centrally manage the real time status and historical status of each cart 408 and/or cabinet 410, as well as identify possible diverters. In essence, the central administrator 400 is capable of monitoring and recording every event that occurs at the medication cart 408 and/or cabinet 410, such as the user access history (i.e., based on user identifier and/or password), battery history, location history (i.e., floor assignment), patient history, etc. Further, the central administrator 400 may differentiate between events, such as differentiate between whether a bin access occurs due to a nurse authentication (i.e., input user identifier and password) or a patient authentication (i.e., patient wristband scan and secondary identifier).

The central administrator 400 may directly interact with the medication carts 408 and/or cabinets 410 (shown by the solid lines directly connecting central administrator 400 and carts 408 and/or cabinets 410) and/or may indirectly interact with the carts 408 and/or cabinets 410 by interacting with a sub-controller system 406, which in turn directly interacts with the carts 408 and/or cabinets 410. For example, the medication carts 408 and/or cabinets 410 may directly interact with a sub-controller system 406 that is located on the floor or ward where the carts 408 and/or cabinets 410 resides. The sub-controller system 406 may be controlled by the central administrator 400, such as the hospital administration system. Information exchanged between the carts 408 and/or cabinets 410 and the central administrator 400 may be routed through the sub-controller system 406 so that additional information (e.g., floor specific information) may be added and/or unnecessary information removed. Further, the central administrator 400 may quickly transfer or exchange information between carts 408 and/or cabinets 410, such as transferring patient information when a patient is transferred between floors.

The information provided to the central administrator 400 may be stored in a database 402, which may be remote from central administrator 400 or included therewith.

The information may be stored for a predetermined amount of time (e.g., store information for a year). Further, central administrator 400 may be coupled with or include a monitoring and reporting system 404 that monitors real-time and historical data about each carts 408 and/or cabinets 410 including: battery status and/or history (charge rate, discharge state, shutdown events), user access (logon, logoff), access events, dispensing history, cancellation history, restocking history, replacement history, bin access/activity (unlock, lock, open, close, and/or other use or diversion data), etc. The monitoring and reporting system 404 may generate one or more email notifications and/or paper reports (e.g., work orders) based on real-time or historical events that occur (or have occurred), such as when a dead battery is detected, low battery is detected, an unauthorized cassette/bin access occurs, a patient medication schedule is missed, excessive and repeated bin access is observed, other diversion data is detected etc. The monitoring and reporting system 404 may further generate one or more reports based on system/cart audits performed. The auditing and/or monitoring parameters for batteries, users, access events, etc. may be predefined in the system so that reports are automatically generated when the parameters are exceeded. For example, the monitoring and reporting system may produce a report related to trends of diversion scores and baseline scores over time as discussed herein.

Because central administrator 400 may be tied to the hospital's ADT, PIS, and/or ADM systems, information input into one of those systems may be immediately available and provided to the medication chart. For example, as medications are provided or updated by a pharmacist, the additions or modifications can immediately or nearly immediately be displayed, via the PIS, on a touch screen of medication carts 408 and/or cabinets 410. Likewise, dosage amounts and/or frequency input into touch screen of carts 408 and/or cabinets 410 may be immediately available to the supervising physician or doctor. Medication cart carts 408 and/or cabinets 410 may be operable with pre-existing hospital systems so that no additional hardware and/or software is needed to integrate medication carts 408 and/or cabinets 410 into the system. Thus, carts 408 and/or cabinets 410 may be essentially plugged into and used with currently operating administration systems.

Figure 5:
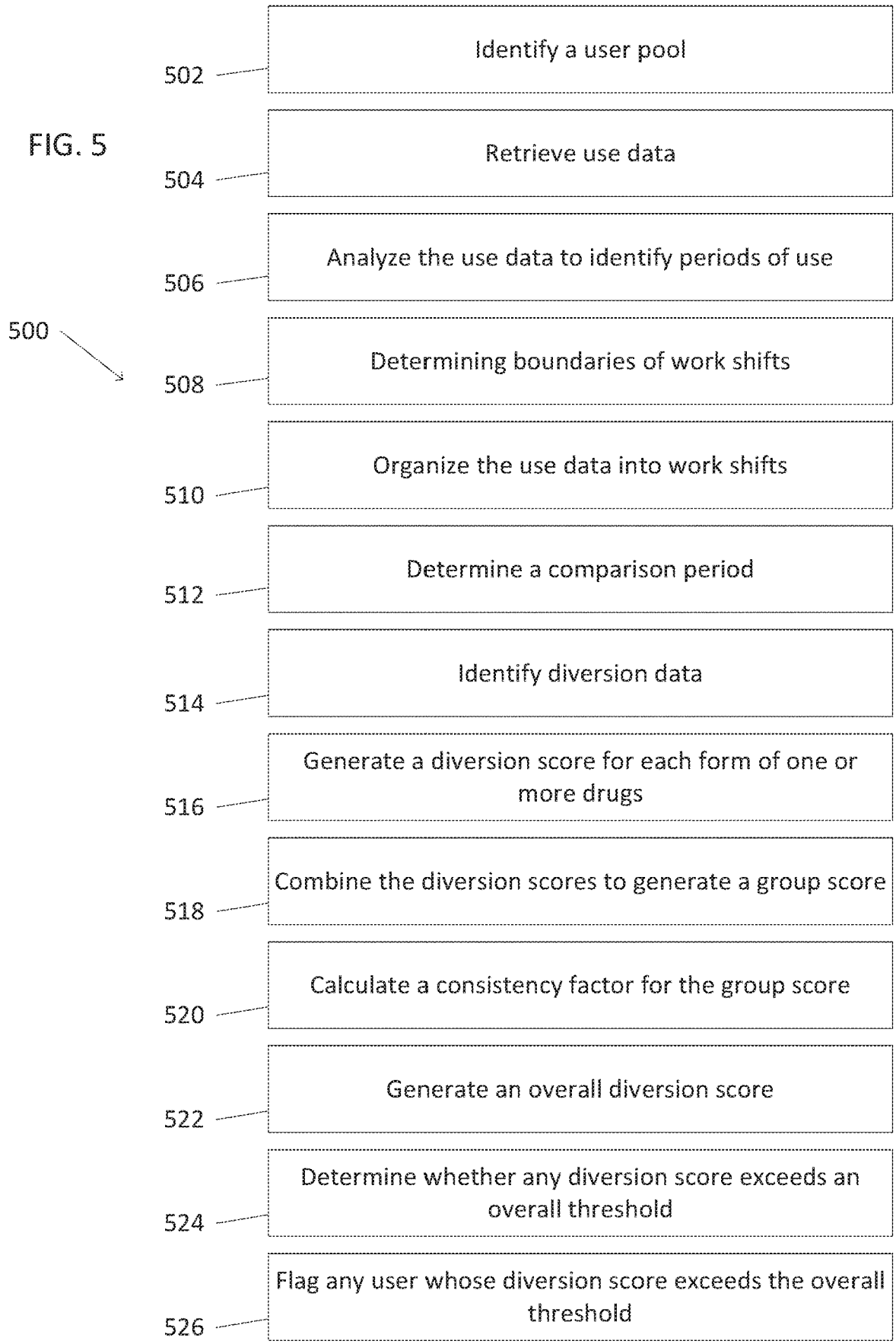
FIG. 5 is a flowchart of a method of identifying possible diverters according to embodiments.

FIG. 5 depicts a flowchart of a process 500 for identifying medical diverters. Process 500 may be executed by a central computer or server of a medical facility. For example, process 500 may be executed by a central administrator in communication with a number of medication dispensing systems, such as central administrator 400 in the system of FIG. 4. The process 500 may be similar to process 300 described above, but may include use data and/or diversion data from multiple medication dispensing systems, allowing for the evaluation of individuals within a larger facility, or within a subset of a facility, such as a single floor or department of the facility. Process 500 may begin with identifying a user pool at block 502. As described above, the user pool may include a number of users having similar job performance functions. The user pool may include medical practitioners that have access to items within a number of medication dispensing systems within a facility. The user pool may be predetermined, such as a group of all nurses that have access to the medication dispensing systems, or may be user-defined such that an administrator may select a particular subset of users to evaluate. For example, the administrator may only wish to evaluate users within the intensive care unit (ICU) of a hospital.

Use data, as described above, may be retrieved for each of the users at block 504. The use data may be retrieved from some or all of the medication dispensing systems within the facility or subset of the facility. In some embodiments, the use data may be communicated to the central administrator in real-time. In other embodiments the use data may be sent periodically, such as in batches at predetermined intervals or upon request when an evaluation of potential diverters is conducted. As noted above, use data may include type and/or quantity of a medication issued, a device and/or supply that a user withdrew from the system, a timestamp, records of returning the supply to the system, records of disposal of a portion of the supply, records of administered dosage amounts, and/or other records related to the dispensing and/or administration of a medication or other medical supply.

At block 506, the use data may be analyzed to identify periods of use of the medication dispensing system for each user within the user pool. For example, the medication dispensing system may monitor timestamps of each use of the medication dispensing system to determine likely periods of work or activity for each user. At block 508, boundaries of work shifts for the user pool may be determined and the use data may be organized into work shifts at block 510. As described above, each work shift may be categorized so that similar types of shifts can be compared across users. It will be appreciated that the disclosed techniques of determining work shifts are illustrative of only some embodiments, and that other techniques may be utilized in accordance with the present invention.

At block 512, a comparison period may be determined. The comparison period includes a time period within which users may be compared. Diversion data may be identified for each user within the comparison period at block 514. The diversion data may be indicative of behavior associated with diversion, such as the diversion of one particular form of one or more medication types, and may include any of the diversion data described herein. A diversion score may be generated for each form of each of the medications at block 516. For example, the diversion data from multiple medication dispensing systems may be aggregated for each user. The diversion data may be averaged based on the number of shifts worked by the user within the comparison period. The diversion data may then be compared statistically with other users' data, such as by using quartile statistics, to determine a diversion score. The diversion score may be indicative of a likelihood that a particular user is diverting medication. A user may have multiple diversion scores, each relating to a specific form of a medication and an indicator of diversion.

At block 518, the diversion scores for all diversion indicators and/or forms of a single medication may be combined for a single user into a group score associated with the single medication. A consistency factor may be calculated for the group score over a span of time at block 520. An overall score may be generated based on a combination of all the group scores, the consistency factors, and/or data from a diversion profile at block 522. The overall score may take into account the type of medication and/or the likelihood that the medication will be subject to diversion. At block 524, a determination whether any user's diversion score exceeds a predetermined threshold may be made. Any user whose diversion score exceeds the predetermined threshold may be flagged as a possible diverter at block 526. As one example, the users whose diversion score is more than 10 may be flagged. Flagged users may be investigated to determine whether the users are actually diverting medications and/or other medical supplies, or whether there is an alternative explanation. In some embodiments, flagging a user may trigger one or more of the medication dispensing systems to lock each flagged user from accessing the medication dispensing systems, or at least a portion of one or more medication dispensing systems corresponding to a medication and/or other medical supply related to a flagged diversion score. For example, the central administrator may communicate a lockout signal over a network to one or more of the medication dispensing systems within a facility. The mediation dispensing systems receiving the lockout signal may then prevent the flagged user or users from unlocking and accessing the medication dispensing systems.

In some embodiments, the group and overall diversion scores may be tracked over time, such as by generating trend data, which may be used to generate a graphical output of trends of overall diversion scores and/or group scores. Upon generation of the overall diversion scores for each user, a trend chart may be generated that includes a history of overall diversion scores for each of the flagged users. Each of the trend charts may be displayed on a remote device, such as a smartphone, laptop, and/or other computing device. An input may be received from the remote device, such as a user of the remote device clicking or otherwise interacting with an icon or other portion of a display of the user device associated with one of the flagged users. A group score trend chart may then be generated that includes a history of the group score for the one of the flagged users, which may then be displayed on the remote device. Further interaction with a group score icon on the remote device may cause a usage chart for the particular type of medication associated with the group score to be shown.

Figure 6:
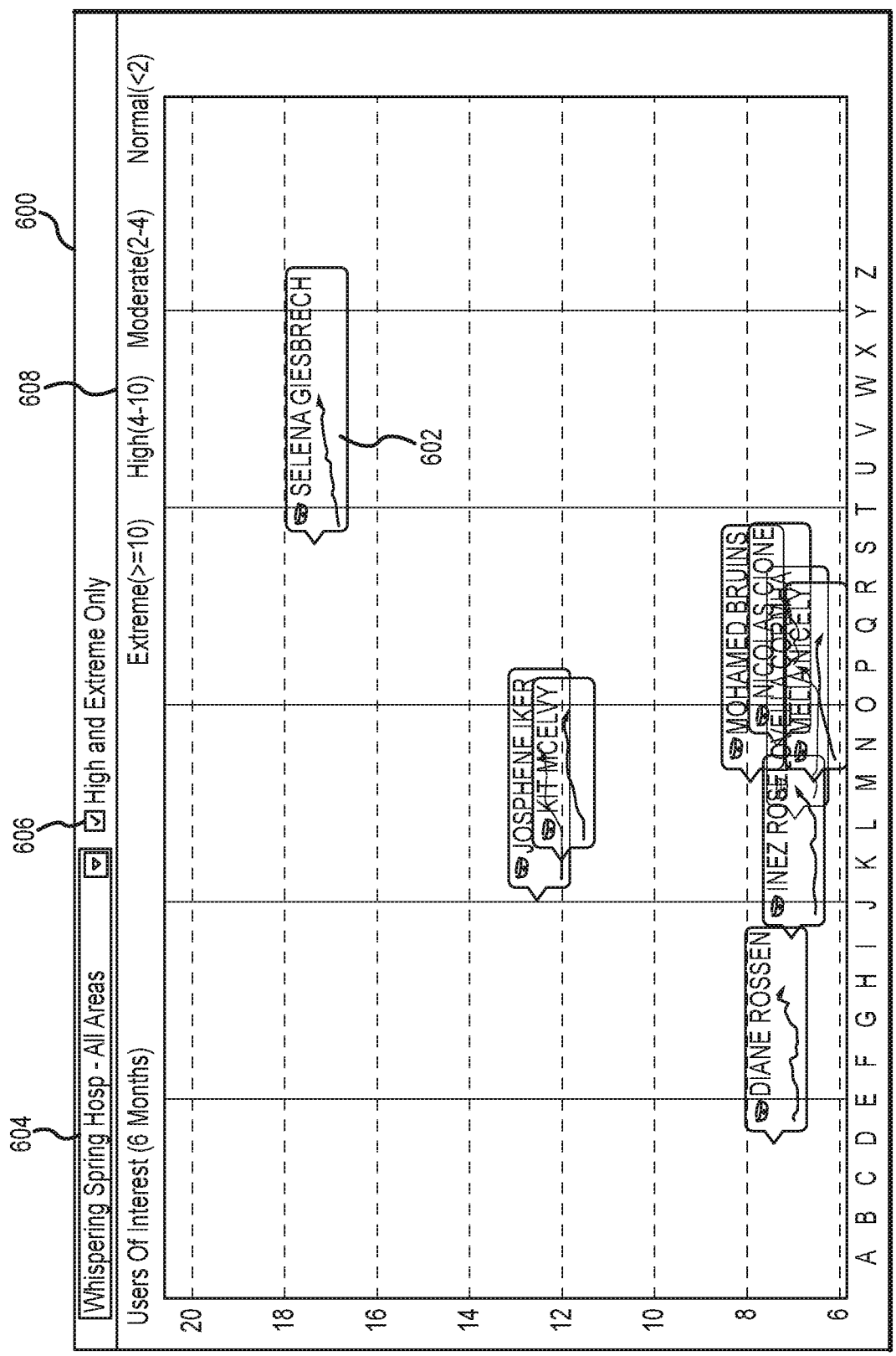
FIG. 6 is a dashboard for viewing overall diversion scores of various users according to the embodiments.

FIG. 6 depicts one embodiment of a dashboard 600 for viewing overall diversion scores of various users. Dashboard 600 may provide a display of overall diversion scores for each user. This may include positioning a trend chart 602 showing a trend or other history of the user's overall diversion score. The dashboard 600 may include a location or facility filter 604 that enables a person accessing the dashboard 600 to select a particular hospital, facility, and/or portion of a facility for which diversion scores are to be displayed. The dashboard 600 may also include a threshold filter 606 that enables a person accessing the dashboard 600 to select a threshold for viewing users. For example, the person may choose to view only high or extreme diversion risk users based on a threshold scale 608. Threshold scale 608 may serve as a key that indicates diversion risk ranges that each of the users may fall within.

Figure 7:
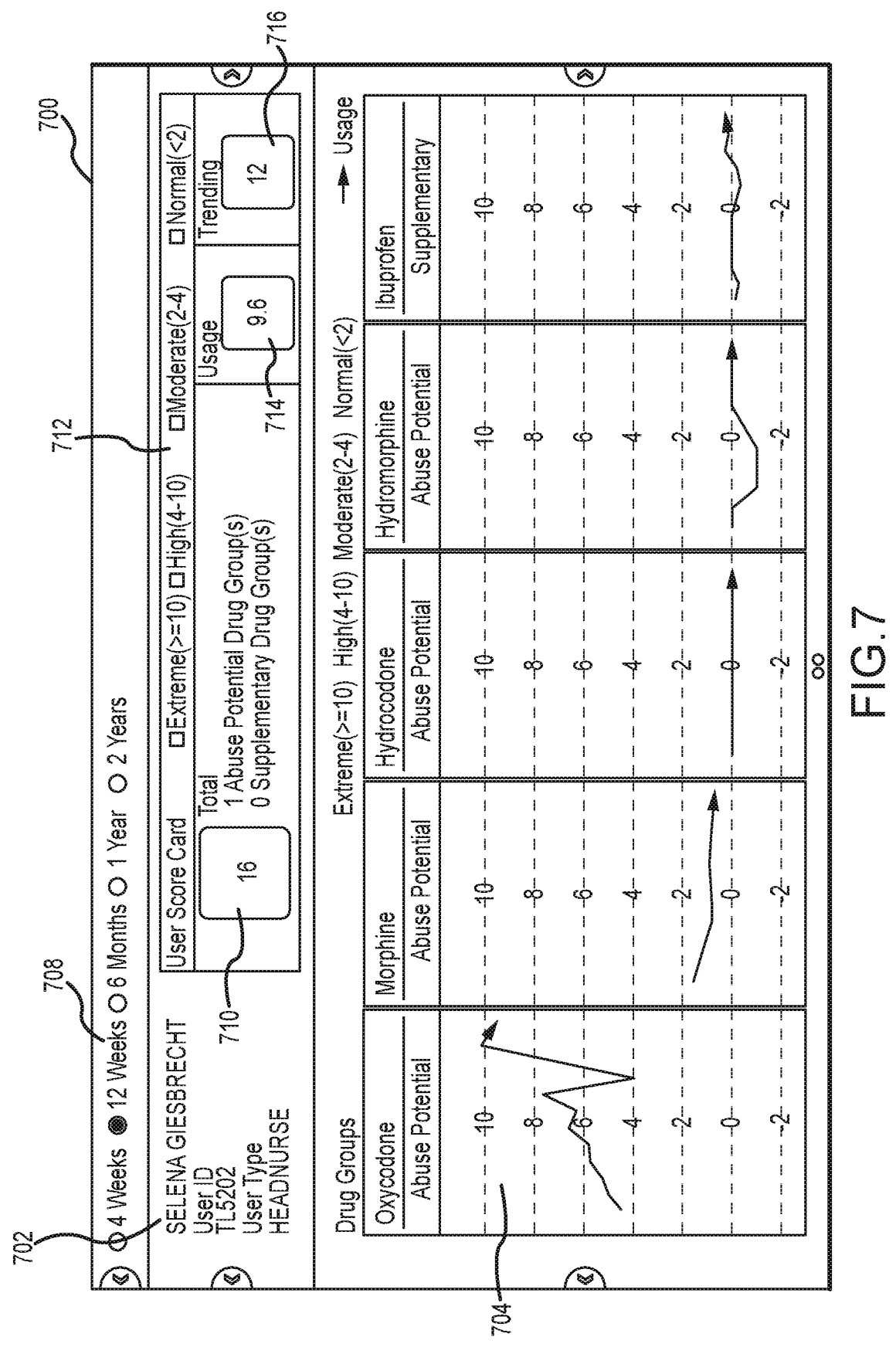

FIG. 7 depicts one embodiment of a dashboard 700 for viewing group scores 704 for various drugs of a selected user 702. In some embodiments, dashboard 700 may be accessed when the person interacts with dashboard 600. For example, the person may click or otherwise interact with the selected user's 702 trend chart 602 and/or icon or button associated therewith. The group score 704 may include a trend chart for various types of medications, with each trend chart providing a representation of a history of the group score 704. In some embodiments, certain medication types may be highlighted based on a diversion risk. The diversion risk may be based on the group score exceeding a threshold and/or having an upward trend. Dashboard 700 may include a timeframe filter 708 that allows a person accessing the dashboard 700 to select a date range or other time period to view group score trends. Dashboard 700 may also include a user score card for the selected user 702. The user score card may include the user's overall diversion score 710, a threshold scale 712, a usage score 714 indicative of a diversion risk based on the selected user's 702 diversion score, and/or a trend score 716 indicative of the selected user's 702 trends or consistency factor for particular group scores 704.

FIG. 8 depicts one embodiment of a dashboard 800 for viewing interactions with a particular medication type for a selected user. In some embodiments, dashboard 800 may be accessed when the person interacts with dashboard 700. For example, the person may click or otherwise interact with the particular medication type's group score 704 and/or icon or button associated therewith. Dashboard 800 may show a user 802 who issued and/or otherwise interacted with the particular medication type. The interactions may be associated with one or more patients 804. Dashboard 800 may also include a timeframe filter 806 that allows a person accessing the dashboard 800 to select a date range or other time period to view interactions of the particular medication type. Dashboard 800 may further include a drug section 808 that indicates a particular form of the medication type involved in each interaction. A notable events section 810 may be included that indicates when a possible diversion event and/or other diversion data is associated with an interaction. Notable events section 810 may include information detailing the nature of a particular diversion event. Additional information may be included in dashboard 800. For example, a timestamp of each interaction, an amount of drug issued in each interaction, data related to whether a drug was wasted and/or returned, data from a medication order, an interval of time between doses of the drug, a number of doses over a period of time, and/or other information relevant to detecting diversion of the medication type may be included on dashboard 800.

Figure 9:
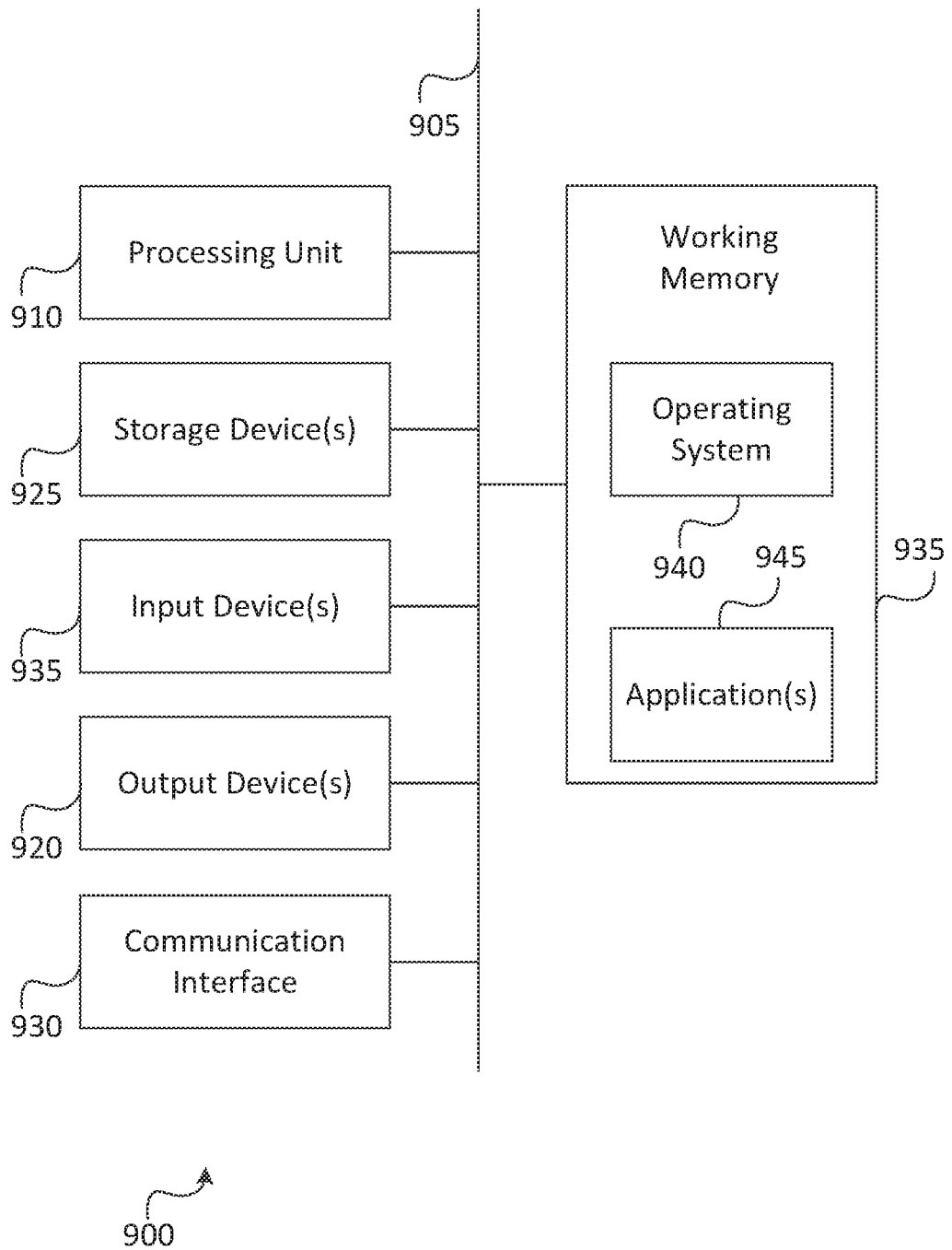
FIG. 9 is a block diagram of an exemplary computer system capable of being used in at least some portion of the apparatuses or systems of the present invention, or implementing at least some portion of the methods of the present invention.

A computer system as illustrated in FIG. 9 may be incorporated as part of the previously described computerized devices. For example, computer system 900 can represent some of the components of the cart 10 and 408, cabinet 200 and 410, central administrator 400 as described herein. FIG. 9 provides a schematic illustration of one embodiment of a computer system 900 that can perform the methods provided by various other embodiments, as described herein, and/or can function as the host computer system, a remote kiosk/terminal, a ticket vending machine or other point-of-sale device, a mobile device, and/or a computer system. FIG. 9 is meant only to provide a generalized illustration of various components, any or all of which may be utilized as appropriate. FIG. 9, therefore, broadly illustrates how individual system elements may be implemented in a relatively separated or relatively more integrated manner.

The computer system 900 is shown comprising hardware elements that can be electrically coupled via a bus 905 (or may otherwise be in communication, as appropriate). The hardware elements may include a processing unit 910, including without limitation one or more general-purpose processors and/or one or more special-purpose processors (such as digital signal processing chips, graphics acceleration processors, and/or the like); one or more input devices 915, which can include without limitation a mouse, a keyboard, a touchscreen, receiver, a motion sensor, a camera, a smartcard reader, a contactless media reader, and/or the like; and one or more output devices 920, which can include without limitation a display device, a speaker, a printer, a writing module, and/or the like.

The computer system 900 may further include (and/or be in communication with) one or more non-transitory storage devices 925, which can comprise, without limitation, local and/or network accessible storage, and/or can include, without limitation, a disk drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data stores, including without limitation, various file systems, database structures, and/or the like.

The computer system 900 might also include a communication interface 930, which can include without limitation a modem, a network card (wireless or wired), an infrared communication device, a wireless communication device and/or chipset (such as a Bluetooth™ device, an 502.11 device, a WiFi device, a WiMax device, an NFC device, cellular communication facilities, etc.), and/or similar communication interfaces. The communication interface 930 may permit data to be exchanged with a network (such as the network described below, to name one example), other computer systems, and/or any other devices described herein. In many embodiments, the computer system 900 will further comprise a non-transitory working memory 935, which can include a RAM or ROM device, as described above.

The computer system 900 also can comprise software elements, shown as being currently located within the working memory 935, including an operating system 940, device drivers, executable libraries, and/or other code, such as one or more application programs 945, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 925 described above. In some cases, the storage medium might be incorporated within a computer system, such as computer system 900. In other embodiments, the storage medium might be separate from a computer system (e.g., a removable medium, such as a compact disc), and/or provided in an installation package, such that the storage medium can be used to program, configure and/or adapt a general purpose computer with the instructions/code stored thereon. These instructions might take the form of executable code, which is executable by the computer system 900 and/or might take the form of source and/or installable code, which, upon compilation and/or installation on the computer system 900 (e.g., using any of a variety of generally available compilers, installation programs, compression/decompression utilities, etc.) then takes the form of executable code.

Substantial variations may be made in accordance with specific requirements. For example, customized hardware might also be used, and/or particular elements might be implemented in hardware, software (including portable software, such as applets, etc.), or both. Moreover, hardware and/or software components that provide certain functionality can comprise a dedicated system (having specialized components) or may be part of a more generic system. For example, a risk management engine configured to provide some or all of the features described herein relating to the risk profiling and/or distribution can comprise hardware and/or software that is specialized (e.g., an application-specific integrated circuit (ASIC), a software method, etc.) or generic (e.g., processing unit 910, applications 945, etc.) Further, connection to other computing devices such as network input/output devices may be employed.

Some embodiments may employ a computer system (such as the computer system 900) to perform methods in accordance with the disclosure. For example, some or all of the procedures of the described methods may be performed by the computer system 900 in response to processing unit 910 executing one or more sequences of one or more instructions (which might be incorporated into the operating system 940 and/or other code, such as an application program 945) contained in the working memory 935. Such instructions may be read into the working memory 935 from another computer-readable medium, such as one or more of the storage device(s) 925. Merely by way of example, execution of the sequences of instructions contained in the working memory 935 might cause the processing unit 910 to perform one or more procedures of the methods described herein.

The terms "machine-readable medium" and "computer-readable medium," as used herein, refer to any medium that participates in providing data that causes a machine to operate in a specific fashion. In an embodiment implemented using the computer system 900, various computer-readable media might be involved in providing instructions/code to processing unit 910 for execution and/or might be used to store and/or carry such instructions/code (e.g., as signals). In many implementations, a computer-readable medium is a physical and/or tangible storage medium. Such a medium may take many forms, including but not limited to, non-volatile media, volatile media, and transmission media. Non-volatile media include, for example, optical and/or magnetic disks, such as the storage device(s) 925. Volatile media include, without limitation, dynamic memory, such as the working memory 935. Transmission media include, without limitation, coaxial cables, copper wire and fiber optics, including the wires that comprise the bus 905, as well as the various components of the communication interface 930 (and/or the media by which the communication interface 930 provides communication with other devices). Hence, transmission media can also take the form of waves (including without limitation radio, acoustic and/or light waves, such as those generated during radiowave and infrared data communications).

Common forms of physical and/or tangible computer-readable media include, for example, a magnetic medium, optical medium, or any other physical medium with patterns of holes, a RAM, a PROM, EPROM, a FLASH-EPROM, any other memory chip or cartridge, a carrier wave as described hereinafter, or any other medium from which a computer can read instructions and/or code.

The communication interface 930 (and/or components thereof) generally will receive the signals, and the bus 905 then might carry the signals (and/or the data, instructions, etc. carried by the signals) to the working memory 935, from which the processor(s) 905 retrieves and executes the instructions. The instructions received by the working memory 935 may optionally be stored on a non-transitory storage device 925 either before or after execution by the processing unit 910.

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

What is claimed is:

1. A medication dispensing system for identifying medical diverters, the medication dispensing system comprising:
   an interior comprising a plurality of compartments where items are stored;
   a plurality of doors providing access to the plurality of compartments of the interior;
   a plurality of mechanical locking mechanisms, wherein at least one of the plurality of mechanical locking mechanisms is engaged to secure at least one of the plurality of doors, each mechanical locking mechanism being configured to physically lock the at least one of the plurality of doors in a closed position, wherein in the closed position the at least one of the plurality of doors prevents access to at least one of the plurality of compartments of the interior;
   a communications interface that is in communication with an additional medication dispensing system that is remotely located from the medication dispensing system; and
   a computing device, the computing device comprising:
      a memory; and;
      a processor configured to:
         identify a user pool, the user pool comprising a plurality of users having similar job performance functions;
         retrieve use data for each of the plurality of users from the medication dispensing system, wherein the use data is indicative of when each user accesses the medication dispensing system;
         analyze the use data to identify periods of use of the medication dispensing system for each user within the user pool;
         determine boundaries of work shifts for each user based on the periods of use;
         organize the use data into work shifts, wherein each work shift defines a contiguous period of time that a particular user of the plurality of users worked;
         determine a comparison period comprising a time period within which users of the user pool may be compared;
         identify diversion data for each user within the comparison period, the diversion data being indicative of behavior associated with diversion of one of a plurality of particular forms of at least one medication type;
         generate a diversion score for each of the plurality of particular forms of the at least one medication type by averaging the diversion data per number of work shifts worked for each user during the comparison period and statistically comparing the averaged diversion data for the plurality of users to calculate the diversion score, the diversion score being indicative of a likelihood that a particular user is diverting a particular one of the plurality of particular forms of the at least one medication type;
         combine the diversion scores for each of the plurality of particular forms of the at least one medication type for a single user within the comparison period to generate a group score for the single user, the group score associated with the at least one medication type;
         generate a group threshold based on group scores for the plurality of users;
         update the group score and the group threshold over each of a plurality of work shifts;
         track the group scores from each of the plurality of work shifts against the group thresholds from each of the plurality of work shifts over a period of time representing the plurality of work shifts;
         generate an overall diversion score based at least in part on the group scores for each of the at least one medication type and a diversion profile of the at least one medication type;
         determine whether any user's overall diversion score exceeds an overall threshold;
         flag any user whose overall diversion score exceeds the overall threshold as a possible diverter;
         lock any flagged users out of at least one of the plurality of compartments of the interior of the medication dispensing system that is associated with the at least one medication type by actuating at least one of the plurality of mechanical locking mechanisms of the medication dispensing system to move the at least one of the plurality of mechanical locking mechanisms into a locked position such that the any flagged users do not have physical access to the at least one of the plurality of compartments of the interior that is associated with the at least one medication type; and
         transmit over a network, using the communications interface, a lockout signal to the additional medication dispensing system that causes the additional medication dispensing system to lock the any flagged users out of the additional medication dispensing system by causing the actuation of an additional mechanical locking mechanism of the additional medication dispensing system to move the additional mechanical locking mechanism into a locked position such that the any flagged users do not have physical access to at least a portion of an interior of the additional medication dispensing system that is associated with the at least one medication type.

2. The medication dispensing system for identifying medical diverters of claim 1, wherein:
the diversion data comprises one or more of a number of instances an issuance of one of the plurality of particular forms of the at least medication type was inconsistent with a medical order, a number of instances one of the plurality of particular forms of the at least medication type was issued to a patient who should have been discharged, or a number of times a high amount or excessive amount of one of the plurality of particular forms of the at least medication type was issued.

3. The medication dispensing system for identifying medical diverters of claim 1, wherein:
the diversion data is related to issuance of one of the plurality of particular forms of the at least medication type.

4. The medication dispensing system for identifying medical diverters of claim 3, wherein the processor is further configured to:
generate a trend chart comprising a history of overall diversion scores for each of the flagged users; and
cause each of the trend charts to be displayed on a remote device.

5. The medication dispensing system for identifying medical diverters of claim 4, wherein the processor is further configured to:
receive an input from the remote device, the input being associated with one of the flagged users;
generate group score trend chart comprising a history of the group score for the one of the flagged users; and
cause the group score trend chart to be displayed on the remote device.

6. The medication dispensing system for identifying medical diverters of claim 1, wherein the processor is further configured to:
retrieve a plurality of medical orders relating to medications issued from the medication dispensing system; and
analyze ordered medications from the plurality of medical orders against actual issuance of medications to identify instances of issuance of medications that were inconsistent with the plurality of medical orders.

7. The medication dispensing system for identifying medical diverters of claim 1, wherein:
identifying diversion data for each user comprises comparing an amount of a particular drug dispensed from the medication dispensing system with medical documentation to identify the diversion data comprising discrepancies between the amount and the medical documentation.

8. The medication dispensing system for identifying medical diverters of claim 1, wherein the processor is further configured to:
generate trend data for one or more of the diversion scores, the group scores, or the overall diversion scores for each user; and
produce a graphical output of the trend data.

9. The medication dispensing system for identifying medical diverters of claim 1, wherein:
the use data comprises one or more of a timestamp of a use, a record of an issuance of a particular drug, or a record of a cancellation of an issuance of the particular drug.

10. The medication dispensing system for identifying medical diverters of claim 1, wherein:
the diversion data is only identified for a particular subset of medications and supplies.

11. A method for identifying medical diverters, the method comprising:
identifying a user pool, the user pool comprising a plurality of users having similar job performance functions;
retrieving use data for each of the plurality of users from a medication dispensing system, wherein the use data is indicative of when each user accesses the medication dispensing system;
analyzing the use data to identify periods of use of the medication dispensing system for each user within the user pool;
determining boundaries of work shifts for each user based on the periods of use;
organizing the user pool into work shifts, wherein each work shift defines a contiguous period of time that a particular user of the plurality of users worked;
determining a comparison period comprising a time period within which users of the user pool may be compared;
identifying diversion data for each user within the comparison period, the diversion data being indicative of behavior associated with diversion of one of a plurality of particular forms of at least one medication type;
generating a diversion score for each of the plurality of particular forms of the at least one medication type by averaging the diversion data per number of work shifts worked for each user within the work shift during the comparison period and statistically comparing the averaged diversion data for the plurality of users to calculate the diversion score, the diversion score being indicative of a likelihood that a particular user is diverting a particular one of the plurality of particular forms of the at least one medication type;
combining the diversion scores for each of the plurality of particular forms of the at least one medication type for a single user within the comparison period to generate a group score for the single user, the group score associated with the at least one medication type;
generating a group threshold based on group scores for the plurality of users;
updating the group score and the group threshold over each of a plurality of work shifts;
tracking the group scores from each of the plurality of work shifts against the group thresholds from each of the plurality of work shifts over a period of time representing the plurality of work shifts;
generating an overall diversion score based at least in part on the group scores for each of the at least one medication type and a diversion profile of the at least one medication type;
determining whether any user's overall score exceeds an overall threshold;
flagging any user whose diversion score exceeds the overall threshold as a possible diverter;
locking any flagged users out of the medication dispensing system by causing the actuation of a mechanical locking mechanism of the medication dispensing system to move the mechanical locking mechanism into a locked position such that the any flagged users do not have physical access to at least a portion of an interior of the medication dispensing system that is associated with the at least one medication type; and transmitting over a network, a lockout signal to an additional medication dispensing system that is located remotely from the medication dispensing system that causes the additional medication dispensing system to lock the any flagged users out of the additional medication dispensing system by causing the actuation of an additional mechanical locking mechanism of the additional medication dispensing system to move the additional mechanical locking mechanism into a locked position such that the any flagged users do not have physical access to at least a portion of an interior of the additional medication dispensing system that is associated with the at least one medication type.

12. The method for identifying medical diverters of claim 11, wherein:

the diversion data comprises one or more of a number of instances an issuance of one of the plurality of particular forms of the at least medication type was inconsistent with a medical order, a number of instances one of the plurality of particular forms of the at least medication type was issued to a patient who should have been discharged, or a number of times a high amount or excessive amount of one of the plurality of particular forms of the at least one medication type was issued.

13. The method for identifying medical diverters of claim 11, wherein:

the diversion data is related to issuance of one of the plurality of particular forms of the at least medication type.

14. The method for identifying medical diverters of claim 13, further comprising:

generating a trend chart comprising a history of overall diversion scores for each of the flagged users; and causing each of the trend charts to be displayed on a remote device.

15. The method for identifying medical diverters of claim 14, further comprising:

receiving an input from the remote device, the input being associated with one of the flagged users;

generating group score trend chart comprising a history of the group score for the one of the flagged users; and causing the group score trend chart to be displayed on the remote device.

16. The method for identifying medical diverters of claim 11, further comprising:

retrieving a plurality of medical orders relating to medications issued from the medication dispensing system; and analyzing ordered medications from the plurality of medical orders against actual issuance of medications to identify instances of issuance of medications that were inconsistent with the plurality of medical orders.

17. The method for identifying medical diverters of claim 11, wherein:

identifying diversion data for each user comprises comparing an amount of a particular drug dispensed from the medication dispensing system with medical documentation to identify the diversion data comprising discrepancies between the amount and the medical documentation.

18. The method for identifying medical diverters of claim 11, further comprising:

generating trend data for one or more of the diversion scores, the group scores, or the overall diversion score for each user; and producing a graphical output of the trend data.

19. The method for identifying medical diverters of claim 11, wherein:

the use data comprises one or more of a timestamp of a use, a record of an issuance of a particular drug, or a record of a cancellation of an issuance of the particular drug.

* * * * *